(12) United States Patent
Ekström et al.

(10) Patent No.: US 10,182,888 B2
(45) Date of Patent: Jan. 22, 2019

(54) FASTENING SYSTEM FOR DENTAL IMPLANTS (71) Applicant: Addbutment Dental AB, Lund (SE)

(72) Inventors: Bo Ekström, Bunkeflostrand (SE); Christian Lauridsen, Limhamn (SE)

(73) Assignee: Addbutment Dental AB, Lund (SE)

( * ) Notice: Subject to any disclaimer, the term of this patent is extended or adjusted under 35 U.S.C. 154(b) by 0 days.

(21) Appl. No.: 15/301,582

(22) PCT Filed: Apr. 7, 2015

(86) PCT No.: PCT/SE2015/050418
§ 371 (c)(1),
(2) Date: Oct. 3, 2016

(87) PCT Pub. No.: WO2015/152815
PCT Pub. Date: Oct. 8, 2015

(65) Prior Publication Data
US 2017/0105819 A1    Apr. 20, 2017

(30) Foreign Application Priority Data

Apr. 4, 2014    (SE) ...................................... 1450413

(51) Int. Cl.
*A61C 8/00* (2006.01)
(52) U.S. Cl.
CPC .......... *A61C 8/0053* (2013.01); *A61C 8/0048* (2013.01); *A61C 8/0068* (2013.01); *A61C 8/0074* (2013.01)
(58) Field of Classification Search
CPC ..... A61C 8/0048; A61C 8/0053; A61C 8/005; A61C 8/0057; A61C 8/0065;
(Continued)

(56) References Cited

U.S. PATENT DOCUMENTS 5,564,922 A    10/1996  Rosa et al.
5,599,185 A *  2/1997   Greenberg ............. A61C 8/008
                                                       433/173
(Continued)

FOREIGN PATENT DOCUMENTS

EP    2 647 347 A1    10/2013
KR    101065924 B1    9/2011
WO    2012/156459 A1  11/2012

OTHER PUBLICATIONS

Extended European Search Report dated Sep. 14, 2017, issued in corresponding European Application No. EP 15773080.5, filed Apr. 7, 2015, 7 pages.

(Continued)

*Primary Examiner* — Nicholas Lucchesi
*Assistant Examiner* — Shannel Wright
(74) *Attorney, Agent, or Firm* — Christensen O'Connor Johnson Kindness PLLC (57) ABSTRACT

A fastening system (100) for a dental implant (30) comprising a ball shaped portion (31), wherein the fastening system (100) comprises a body (12) having a seat (10, 20) forming a cavity. The fastening system is characterized in that the body (12) comprises at least two parts (10a, 10b, 20a, 20b) together forming the seat (10, 20). The parts (10a, 10b, 20a, 20b) are arranged such that the seat (10, 20) can engage around the ball shaped portion (31) of the dental implant (30) and in that the seat (10, 20) is movable between a first position in which the parts (10a, 10b, 20a, 20b) are allowed to move relative each other, and a second position in which the parts (10a, 10b, 20a, 20b) are prevented from moving relative each other.

18 Claims, 4 Drawing Sheets (58) Field of Classification Search
CPC ..... A61C 8/0068; A61C 8/0074; A61C 8/008; A61C 8/0069; A61C 8/0072; A61C 8/0093; A61C 13/265–13/2656; A61C 13/2653; A61C 8/0079
See application file for complete search history.

(56) References Cited

U.S. PATENT DOCUMENTS

| | | | |
|---|---|---|---|
| 5,842,864 A | 12/1998 | Unger | |
| 5,871,357 A * | 2/1999 | Tseng | A61C 13/235 433/177 |
| 6,190,169 B1 * | 2/2001 | Bluemli | A61C 13/2656 433/172 |
| 2007/0233116 A1 * | 10/2007 | Olerud | A61B 17/8047 606/86 A |
| 2014/0017631 A1 * | 1/2014 | Benzon | A61C 8/0053 433/173 |
| 2014/0178837 A1 * | 6/2014 | Benzon | A61C 8/0053 433/173 |
| 2015/0323690 A1 * | 11/2015 | Popadynetz | G01V 1/24 702/14 |

OTHER PUBLICATIONS

International Search Report and Written Opinion dated Jul. 15, 2015, issued in corresponding International Application No. PCT/SE2015/050418, filed Apr. 7, 2015, 10 pages.

* cited by examiner

FASTENING SYSTEM FOR DENTAL IMPLANTS

TECHNICAL FIELD

The present invention relates to a fastening system for a dental implant. More particularly, the present invention relates to a fastening system having a seat arranged to form a ball joint, with a ball shape of a dental implant.

BACKGROUND

Implant systems of today attempt to restore the patient to normal function, comfort, aesthetic, speech and health regardless of the current oral condition. These implant systems are based on the implantation of dental implants, such as dental implants made of biocompatible titanium or any other dental material, through insertion into the patient's jawbone. There are many methods to attach a dental superstructure to an implant, where one example is the use of dental cement. Other examples are methods that are based on the use of a screw means, where these screw members can attach the superstructure to the implant, either directly or via spacers.

When a patient has been without tooth/teeth for a period of time, the jawbone starts to degenerate, since the jawbone is not under strain from masticatory forces. This results in less bone material for the proper anchoring of a dental implant. To find enough bone for optimal implantation, the dental implant sometimes has to be angled so that the longitudinal axis of the dental implant projects out of the mouth.

Fixing a superstructure with dental cement is complicated due to various factors such as varied drying time of the cement, difficulties in fixating the superstructure while the dental cement is drying, and problems related to adjusting a dental superstructure once the dental cement has dried. If a screw means is used, it necessitates that the mouth of the screw channel is placed on a visual surface of the dental superstructure. Also, the optimum placement of the implant, due to the present dental situation, often results in a non-optimal placement of the dental superstructure in terms of the patients aesthetics, phonetics and bite. Furthermore, it is complicated to manufacture superstructures adapted for dental implants with diverting securing angles, since spacers and/or integrated spacers have to be exactly configured in respect of the different angles of the dental implants. This may also result in a complicated mounting procedure of the superstructure, if two closely located dental implants deviant directions.

The means already known in the art for achieving this goal include the use of angled spacers and dental superstructures attached to the implant with adhesive or with other techniques not based on the use of a screw member. The angled spacers have many drawbacks and are characterized by adding significant height to the superstructure. It also results in an increased complexity of the attachment of the superstructure to the implant.

Furthermore, when an implant has already been implanted, and a satisfactory osseointegration of the implant has been obtained, it would be of great damage to exchange such an implant with another implant, better suited for attachment of structures or spacer elements needed in changed circumstances for the patient. This may be the case if the patient is in need of some kind of reconstruction of the dental structure, such as for example in case of loosing yet another tooth. In this case it would be better to have a dental implant better suited for adaptation in respect of other implants, spacer elements, and/or superstructures in the mouth of the patient.

Hence, an improved fastening system for dental implant and superstructure would be advantageous, and in particular a fastening system allowing for a good fit of the dental implant and the superstructure to the gum. Furthermore, a simpler, faster and cheaper production method of the fastening system as well as cost-effectiveness, more simple assembly allowing for greater freedom of placement of a dental implant would be advantageous. This enables use of an implant that could be placed optimally with regard to the dental situation, i.e. the anatomy of the jawbone, while still allowing the dental superstructure to be applied in an optimal way to the implant.

SUMMARY

Accordingly, the present invention preferably seeks to mitigate or eliminate one or more of the above-identified deficiencies in the art singly or in any combination and solves at least the above mentioned problems by providing a fastening system for dental implants and superstructures.

According to a first aspect a fastening system for a dental implant comprising a ball shaped portion is provided. The fastening system comprises a body having a seat forming a cavity, characterized in that the body comprises at least two parts together forming the seat, wherein the parts are arranged such that the seat can engage around the ball shaped portion of the dental implant and in that the parts are movable between a first position in which the parts are allowed to move relative each other, and a second position in which the parts are prevented to move relative each other.

In the first position, in which the parts are allowed to move relative each other for expanding the dimensions of the seat, the seat may receive a ball-shape of a dental implant. In the second position, in which the parts are not allowed to move relative each other the inserted ball-shape is locked within the seat.

The seat may form a spherical cavity and the seat may have a radius that is slightly greater than, or equal to, the radius of the ball shaped portion of the dental implant. Furthermore, the body forming the seat may be connected to a screw means for maneuvering the position of the parts forming the seat.

The screw means may be arranged in a channel or in a screw hole in a superstructure in order to fasten the fastening system to the superstructure. Hence, the fastening system may form part of a superstructure.

The body forming the seat may be movable in the longitudinal direction along a tapered inner structure of the screw means between the first and the second position.

The parts of the seat may be movable relative each other in a horizontal direction when the seat is in the first position, such that the seat can receive the ball shaped portion of the dental implant.

According to a further aspect a fastening system arranged to form a socket together with a ball shaped portion of a dental implant is provided. The fastening system comprises a seat forming a cavity. The fastening system is characterized in that the seat comprises at least two parts, wherein the parts are movable from each other such that the seat can engage around the ball shaped portion, and in that the seat is movable between a first position in which the parts are allowed to move from each other, and a second position in which the parts not are allowed to move from each other.

The seat may be movable along a tapering groove in the longitudinal direction between the first and the second position.

The screw means may be arranged in a channel or in a screw hole in a superstructure.

According to a further aspect a superstructure adapted to be arranged to a ball shaped portion of a dental implant is provided. The superstructure comprises a fastening system according to any preceding claims.

According to yet a further aspect a dental implant is provided. The dental implant comprises a ball shaped portion adapted to be arranged to form a socket with a fastening system according to an embodiment of the teachings herein.

According to yet a further aspect a dental implant system is provided. The dental implant system comprises a dental implant comprising a ball shaped portion, a superstructure adapted to be connected to the ball shaped portion of the dental implant and a fastening system according to an embodiment of the teachings herein.

Some embodiments enclosed herein have the benefit of being a simple user-friendly, and cost efficient technique. Further benefits are that the implants are less restricted on where the placement must occur, there is no fixed angles (i.e. 0-45 degrees as in most prior art), no visible screw access holes, no seating problem and the embodiments herein may use standard ball abutments.

BRIEF DESCRIPTION OF THE DRAWINGS

Further objects, features and advantages will appear from the following detailed description, with reference being made to the accompanying drawings, in which:

FIG. 1a-c are schematic views of a fastening system according to one embodiment, where FIG. 1a shows a closed position of the fastening system, FIG. 1b shows an open position of the fastening system, and FIG. 1c shows a further embodiment of the fastening system.

FIG. 2a-b is a schematic view of a body of a fastening system according to one embodiment, where FIG. 2a shows a closed position and FIG. 2b shows an open position;

DETAILED DESCRIPTION

The following description focuses on embodiments applicable to a fastening system for dental implants. For all embodiments described herein, various materials which are suitable for forming a fastening system of dental structures may be used. Further, the fastening system may be manufactured in various ways in accordance with methods being suitable for forming the clamping effect between a seat of a dental superstructure and a ball shaped member of a dental implant.

Figure 1A:
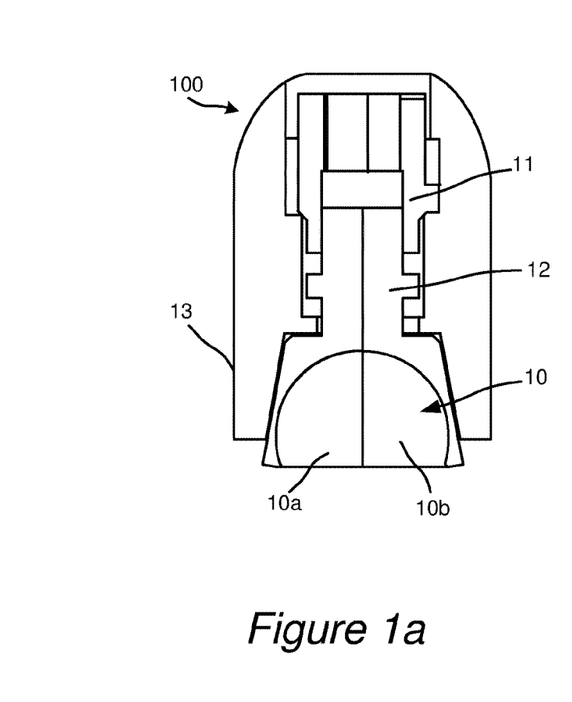

FIG. 1a shows an example of a fastening system 100 adapted to form a ball joint, or a joint socket, together with a ball shaped portion 31 of a dental implant 30. The ball shaped portion 31 is either integrally formed with the implant, or arranged as an abutment on an existing implant. The fastening system 100 is, when in use, provided at a structure that is to be mounted to the implant, and comprises a seat 10 that forms a preferably spherical cavity having a radius slightly greater than, or equal to, the ball shaped portion 31 in order for the seat 10 to grip around the ball shaped portion 31.

Figure 3:
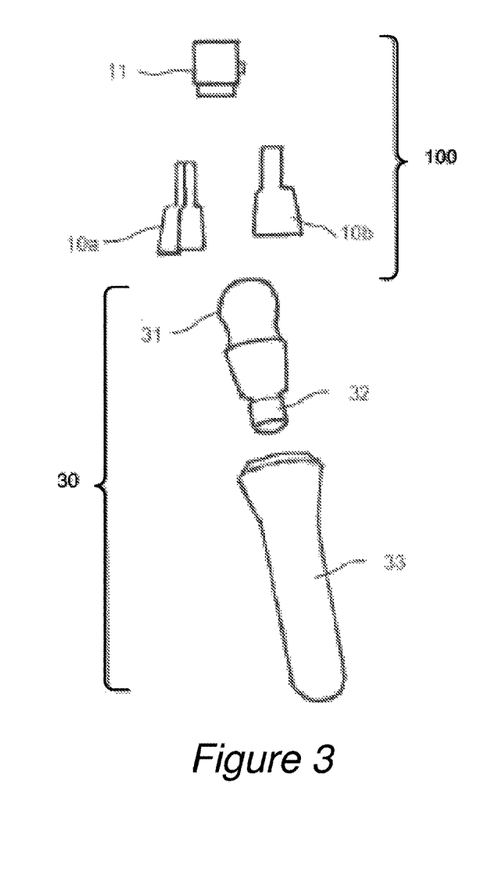
FIG. 3 is an exploded view of a fastening system according to one embodiment, forming a ball joint with a ball shaped portion of a dental implant.
Figure 4:
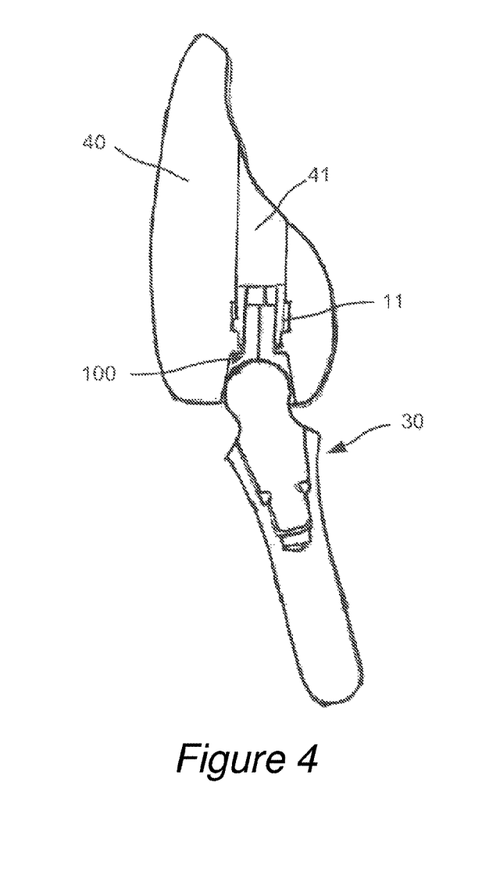
FIG. 4 is a cross sectional view of one embodiment of a fastening system forming a connection between a dental implant and a superstructure.
Figure 5:
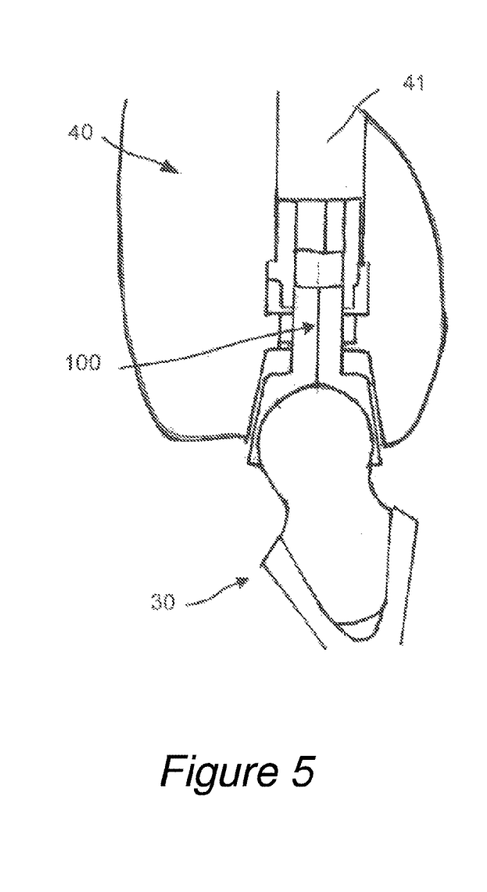
FIG. 5 is a cross sectional view of an embodiment of a fastening system forming a connection between a dental implant and a superstructure.
Figure 6:
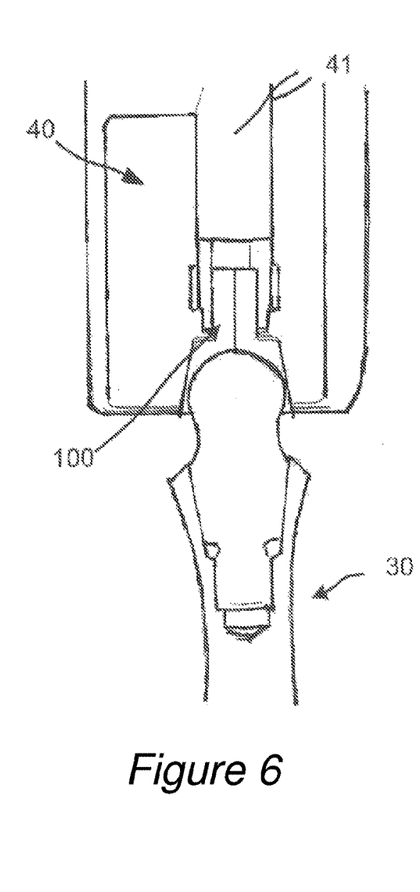
FIG. 6 is a cross sectional view of an embodiment of a fastening system forming a connection between a dental implant and a superstructure.
Figure 7:
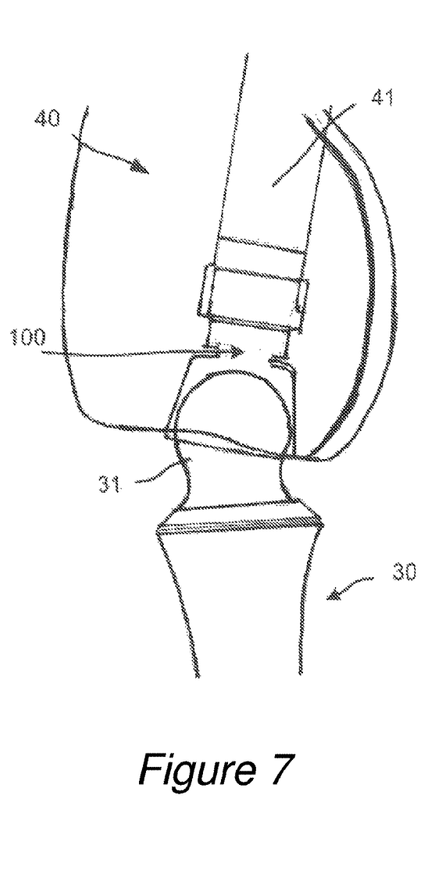
FIG. 7 is a schematic view of an embodiment of a fastening system forming a connection between a dental implant and a superstructure.

The two parts allow the seat 10 to slightly open and thereby clamping the ball shape 31 to the dental implant 30, as described in conjunction to FIG. 3. The clamping effect is achieved by the seat 10 being movable along a tapered groove, for example along a conical recess, in the longitudinal direction. The parts of the seat 10a, 10b can thus be movable from two different positions; position 1 where the seat 10 is open (see FIG. 1b) and position 2 where the seat 10 is closed (see FIG. 1a). When fastening the dental implant 30 the parts of the seat 10a, 10b are pressed above the ball shaped portion 31. Then, the seat 10 is brought upwards in a longitudinal direction in order to secure the fastening with a screw means 11. Although, the seat 10 may be formed as a spherical cavity, the cavity could also be formed in other shapes as long as it is suitable to cause a clamping action around the ball shaped portion 31 and the fastening system prevents the structure having a fastening system from being removed from the ball shaped portion 31 without manipulation of the fastening system 100.

Figure 1B:
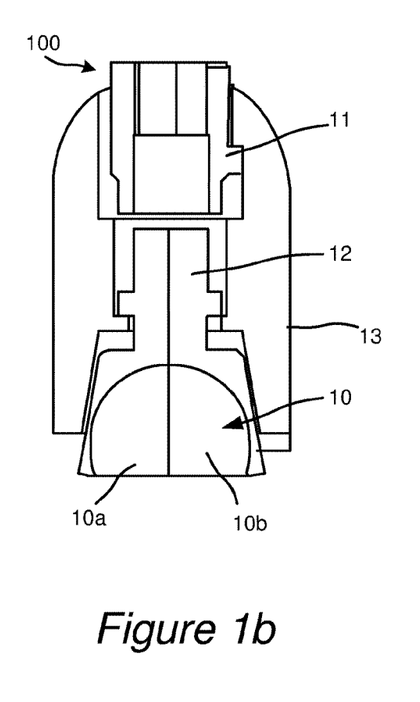

FIG. 1b shows another example of a fastening system 100 adapted to form a socket together with a ball shaped portion 31 of a dental implant 30, where the seat 10 is arranged below its locked position so that the parts 10a, 10b are allowed to separate from each other.

A more detailed description of an embodiment illustrated in FIG. 1a-b, showing fastening system 100 comprising a screw means 11 and a seat 10, is provided below. The fastening system 100 can be arranged either in an opened or a closed position for allowing connection of a ball-shaped member 31 of a dental implant 30, and locking of the ball-shaped member, respectively (shown in FIG. 3).

FIG. 1a shows the fastening system 100 being in a closed position, where the fastening system 100 already has received the ball shaped portion 31 of the dental implant 30. In this position it is not possible to move the received ball shaped portion 31, but the dental implant is locked by means of the fastening system 100. The fastening system 100 comprises a body 12 having at least two parts 10a, 10b together forming a seat. When the fastening system 100 is in a closed position, the parts of the seat 10a, 10b are prevented from moving in a horizontal direction, i.e. away from each other for expanding the dimensions of the seat. Hence, the ball shaped portion 31 being received in the seat 10 is locked.

Locking of the parts 10a, 10b forming the seat 10 is achieved by the provision of a housing 13, in which the parts 10a, 10b forming the seat 10 are received. The housing 13 has a tapered recess, forming a cavity in the shape of a truncated cone. The tapered recess may have a circular cross-section. Similarly, the parts 10a, 10b have an outer surface which forms a tapered body. The taper angle of the body 12 and the recess of the housing 13 are preferably the same. In the position shown in FIG. 1a the outer surface of the body 12 is in contact with the inside surface of the recess of the housing 13. A lateral displacement of the parts 10a, 10b within the recess is thus not possible.

FIG. 1b shows the fastening system 100 being in an open position, where the fastening system 100 is ready to receive the ball shaped portion 31 of the dental implant 30. When the fastening system 100 is in the open position, the parts 10a, 10b forming the seat 10a, 10b are movable relative each other in a horizontal, or lateral direction. This is due to the fact that the parts 10a, 10b have been moved downwards relative the housing 13, such that a circumferential gap is formed between the inner surface of the recess of the housing 13 and the outer surface of the parts 10a, 10b. The spherical cavity formed by the two parts 10a, 10b can receive a ball shaped portion 31 of a dental implant 30 by opening and closing the parts 10a, 10b relative each other. When the two parts of the seat 10 are slightly opened relative each other, the ball shaped portion 31 can easily be arranged in the spherical cavity. This allows the seat to receive the ball shaped portion 31 of the dental implant 30 for forming a ball joint.

When the ball shaped portion 31 is in place, the two parts 10a, 10b are moved towards each other, thus closing the seat around the ball shaped portion 31, and the parts 10a, 10b are subsequently, or simultaneously, lifted upwards relative the housing 13. The gap is consequently continuously reduced during the lifting movement of the parts 10, 10b thus securing the position of the ball-shaped portion relative the seat 10. The fastening system 100 is now in its closed position and the seat 10 is thus clamped around the ball shaped portion 31 of the dental implant 30.

The movement of the parts 10a, 10b of the seat 10 is controlled by adjusting the vertical position of the parts 10a, 10b relative the housing 13. For this, actuating means, preferably in the form of screw means 11, are provided. The screw means 11 are accessible from a side of the fastening system 100 being opposite the end face of the housing 13 having the seat 10, preferably via an open channel of an associated superstructure. When the parts 10a, 10b are in the open position as shown in FIG. 1b, the seat 10 is brought upwards in a longitudinal direction by operating the screw means 11 such that the screw means 11 engages with the parts 10a, 10b. Movement of the screw means 11, and also the parts 10a, 10b, may e.g. be achieved by providing the screw means 11 with external threads cooperating with internal threads of the housing 13.

The body 12 forming the seat 10 is preferably inserted in the recess of the housing 13, and prevented from being dismounted from the housing 13 be means of a flange joint. Hence, the parts 10a, 10b may be provided with a flange, and the housing 13 may have a cooperating flange extending radially inwards such that the flange of the parts 10, 10b may not pass the flange of the housing 13.

Figure 1C:
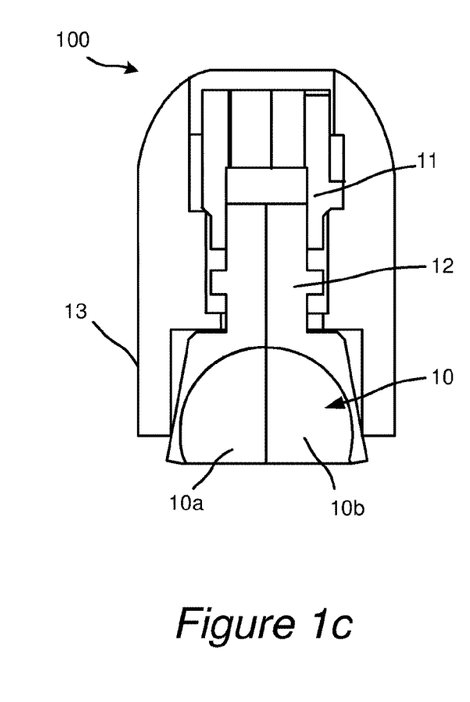

FIG. 1c shows an embodiment of a fastening system 100 where the housing 13 has a recess formed by straight edges. The recess forms a cavity in the shape of a cylinder. In the position shown in FIG. 1c, the outer surface of the body 12 is in contact with the inside surface of the recess of the housing 13. Here the contact is achieved in the lowest part of the housing 13.

Figure 2A:
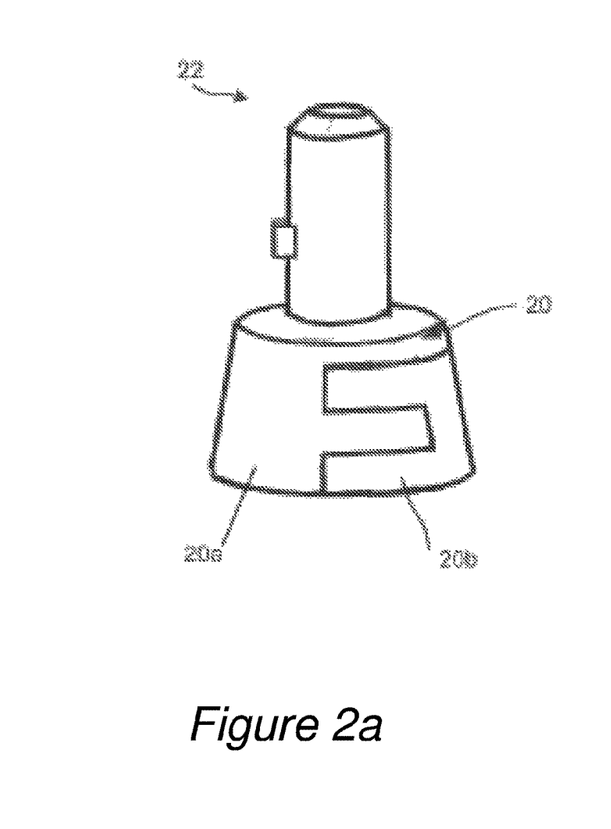
Figure 2B:
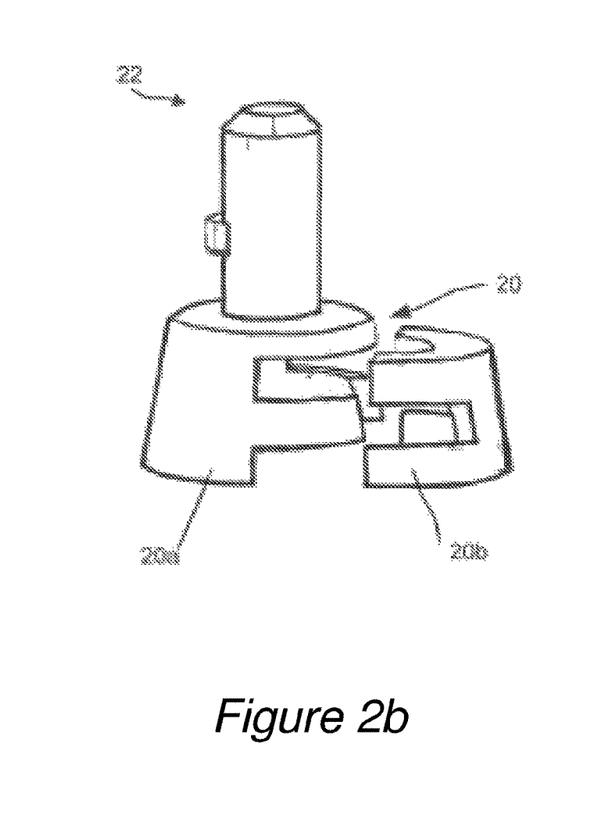

In the embodiment shown in FIG. 2a-b, a body 22 forming a seat 20 comprises two parts 20a, 20b arranged with irregular longitudinal edges is shown. The irregular edges of the two parts may be seen either as a combination of teeth and protrusions, a plurality of indentations or a plurality of protrusions. In the example shown, one part 20a comprises four protrusions extending circumferentially and the other part 20b comprises two protrusions extending circumferentially which are arranged so that they overlap each other when the parts 20a, 20b are fitted together. This allows for a good fixation between the ball shaped portion 31 and the seat 20 and prevents longitudinal movement between the two parts 20a, 20b. The parts 20a, 20b may also be arranged with a plurality of indentations, which when connected are overlapped forming a single seat 20.

It should be understood, that although the embodiments shown in FIG. 2a-b shows protrusions and/or indentations the parts 20a, 20b of the seat could be any type of shape that can engage with each other in order to form a single seat 20. For example, the first part 20a may be a female connector, such as a receptacle, that receives and holds the second male part 20b.

In this exemplified embodiment, the seat 20 is divided into two parts 20a, 20b, but in other embodiments the seat 20 may be split into more parts. The seat 20 is, in this example, formed by two cup-shaped parts than can be opened respectively pressed against each other.

FIG. 3 shows an example of a fastening system 100 adapted to form a socket, or joint, by means of two parts 10a, 10b of a seat 10 together with a ball shaped portion 31 of a dental implant 30. The dental implant 30 comprises a positive spherical surface in the form of a ball 31 and a fastening portion 32 to be anchored in the jawbone. The dental implant 30 is attached to the superstructure 40 through a socket between the ball shaped portion 31 of the implant and the seat 10 in the fastening system 100.

A more detailed description of the embodiment illustrated in FIG. 3, showing a dental implant 30 and a fastening system 100, is provided below. The dental implant 30 has a first and a second end along a longitudinal axis. The dental implant 30 may be in one piece, such as solid or massive, such that there are no interfaces in between the different parts of the dental implant. In the shown example however the dental implant 30 is formed by two separate pieces being secured together to form the implant 30. In another embodiment the dental implant may be formed by any number of parts.

The fastening portion 32 of the dental implant 30 may be anchored directly into the jaw (not shown). However, the dental implant 30 may also comprise a securing portion 33 to which the fastening portion 32 is arranged. The securing portion 33 may then be anchored in the jawbone of a patient. The securing portion may be a threaded portion along its longitudinal axis towards the first end. The anchoring in the jawbone is possible due to osseointegration, well known in the art.

The dental implant further comprises a ball shaped portion 31, for fastening a superstructure (which may consist of an artificial tooth, a human tooth, a prosthesis or any other suitable attachment means as described in conjunction with FIG. 4-7) to said dental implant by means of a fastening system 100, towards the second end of the dental implant 30. The ball shaped portion 31 illustrated in FIG. 3 has a positively spherical shape. The positive spherical shape provides a convex surface area in the second central end of the dental implant. This convex surface area is configured to engagingly interact with the superstructure 40 via the fastening system 100. The radius of the convex surface area may be selected such that it may receive the negative spherical shape, i.e. the negative spherical shape formed by the seat of the two parts 10a, 10b, in the fastening system 100, such that the angle between a central axis of the dental implant does not have to be aligned with a central axis. The superstructure 40 itself may form the housing of the fastening system 100, or the housing may be a separate piece being inserted into the superstructure 40.

FIGS. 4, 5, 6 and 7 shows examples of a fastening system 100 between a dental implant 30 and a superstructure 40. The superstructure 40 may for example consist of an artificial tooth, a human tooth, a prosthesis or a attachment means. A channel or a screw hole is arranged in the superstructure 40 in order to create an opening 41 in the superstructure 40. Hence, the superstructure 40 forms a housing for the fastening system 100. A screw means 11 is arranged in the opening 41 and coupled to the seat 10 in the fastening system 100. The screw means 11 may have one or a plurality of protruding parts arranged to be fixated in the superstructure 40. The screw means 11 may have a conical structure, where the diameter is increasing towards the seat 10. The parts forming the seat 10 are movable in a longitudinal direction relative the screw means, from an open position (see FIG. 1b) to a closed position (see FIG. 1a).

In one embodiment, a lead-through for receiving a sleeve is arranged at the superstructure 40. A part of the lead-through forms an opening 41 in the surface of the superstructure 40.

According to one embodiment, the fastening system 100 is fastened to the osseointegrated dental implant 30 by clamping. Furthermore, the screw means 11 may be fastened to the body 12, which forms the seat 10, by clamping.

The clamping may for example be achieved by resilient materials or by mechanical means. An advantage of resilient materials, such as silicon, is that the resilient materials provide a strong grip. Another advantage is that it facilitates easy application of the dental superstructure by e.g. lower the need for special equipment such as hydraulics, or reducing the number of movable parts used in the construction of the superstructure. An advantage of clamping by mechanical means is ease of use, wherein only simple tools are needed for assembly.

The angle, with which the dental implant 30 is anchored in the jawbone, may be between 0° and 90° in respect of a desired final horizontal axis of the superstructure 40. The desired final horizontal axis is the axis along which it is desired that the superstructure 40 is to be aligned. This may depend on the physical properties of the patient and vary from case to case. The wide range of the angle overcomes the problems related to degeneration of jawbones which may occur when the patient has been without tooth/teeth for a period of time. It is now possible to find an angle which allows the securing portion to find enough bone material to be properly anchored in the jaw and still be suitable for providing support for a superstructure with a specific desired final horizontal axis. Furthermore, the angle-independent connectivity of the superstructure 40 to the dental implant 30 alleviates the need for angular spacers. This in turn allows less complicated installation with fewer parts. Fewer parts may lead to safer mounting of the dental implant, since there are fewer possibilities for the patient to accidentally inhale or otherwise ingest the parts. Furthermore, fewer parts may allow easier assembly.

The ball joint provides the advantage of easy cleaning, since it may be provided without any depressions. Furthermore, since the socket is protruding from the jaw bone, it provides easy access by, e.g. a mould, when making an impression for the positioning of the implant. The socket design also allow angle-independent fitting of a superstructure to multiple sockets. This solution is very suitable for cases where the superstructure is designed to replace all teeth.

The ball shaped portion 31 may be provided with splines, grooves, or in other ways a rugged surface, to increase the friction between the socket or ball joint and another surface adjacently configured thereto.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

The invention claimed is:

1. A fastening system configured to be attached to a ball shaped portion of a dental implant, wherein the fastening system comprises:
    a superstructure forming a housing or a housing being configured to be inserted in a superstructure,
    a body, and
    a screw means,
    wherein the body defines a seat received in a recess of the housing and arranged such that the seat can engage around the ball shaped portion of the dental implant and such that the body is movable between a first position in which the seat is allowed to expand and a second position in which the seat is prevented from expanding,
    wherein the body is movable in a longitudinal direction within the housing between the first and the second position, wherein the body is movable in the longitudinal direction along a tapering inner structure of the housing and/or wherein the body has an outer surface which forms a tapered body,
    wherein the screw means is accessible from a side of the fastening system being opposite an end face of the housing having the seat,
    wherein the body forming the seat is connected to the screw means for maneuvering the position of the body, such that the body is movable in the longitudinal direction relative the screw means from the first position to the second position and such that the seat may be brought upwards in the longitudinal direction by operating the screw means, and
    wherein the screw means is arranged in a channel in the housing or the superstructure.

2. The fastening system according to claim 1, wherein:
    (a) the seat is formed of at least two parts of the body, and
    (b) the at least two parts forming the seat are arranged such that the seat can engage around the ball shaped portion of the dental implant and such that the parts are movable between the first position in which the parts are movable relative to each other and the second position in which the parts are prevented from moving relative to each other.

3. The fastening system according to claim 2, wherein:
    the seat having dimensions; and
    in the first position, in which the parts are allowed to move relative each other for expanding the dimensions of the seat such that the seat may receive the ball shaped portion of the dental implant.

4. The fastening system according to claim 3, wherein in the second position, in which the parts are prevented from moving relative each other the ball shaped portion of the dental implant is locked within the seat.

5. The fastening system according to claim 4, wherein the seat forms a spherical cavity.

6. The fastening system according to claim 5, wherein the seat has a radius that is slightly greater than, or equal to, the radius of the ball shaped portion of the dental implant.

7. The fastening system according to claim 6, wherein the parts of the seat are movable relative each other in a horizontal direction when the seat is in the first position, such that the seat can receive the ball shaped portion of the dental implant.

8. The fastening system according to claim 1, wherein the superstructure is adapted to be arranged to the ball shaped portion of the dental implant, wherein the superstructure comprises the fastening system.

9. A dental implant system comprising:
the fastening system according to claim 1, and
the superstructure adapted to be connected to the ball shaped portion of the dental implant.

10. The fastening system according to claim 2, wherein in the second position, in which the parts are prevented from moving relative each other, the inserted ball shaped portion of the dental implant is locked within the seat.

11. The fastening system according to claim 3, wherein the seat forms a spherical cavity.

12. The fastening system according claim 1, wherein the seat forms a spherical cavity.

13. The fastening system according to claim 4, wherein the seat has a radius that is slightly greater than, or equal to, the radius of the ball shaped portion of the dental implant.

14. The fastening system according to claim 3, wherein the seat has a radius that is slightly greater than, or equal to, the radius of the ball shaped portion of the dental implant.

15. The fastening system according to claim 1, wherein the seat has a radius that is slightly greater than, or equal to, the radius of the ball shaped portion of the dental implant.

16. The fastening system according to claim 4, wherein the parts of the seat are movable relative each other in a horizontal direction when the seat is in the first position, such that the seat can receive the ball shaped portion of the dental implant.

17. The fastening system according to claim 3, wherein the parts of the seat are movable relative each other in a horizontal direction when the seat is in the first position, such that the seat can receive the ball shaped portion of the dental implant.

18. The fastening system according to claim 2, wherein the parts of the seat are movable relative each other in a horizontal direction when the seat is in the first position, such that the seat can receive the ball shaped portion of the dental implant.

* * * * *

UNITED STATES PATENT AND TRADEMARK OFFICE
CERTIFICATE OF CORRECTION

PATENT NO. : 10,182,888 B2
APPLICATION NO. : 15/301582
DATED : January 22, 2019
INVENTOR(S) : B. Ekström et al.

It is certified that error appears in the above-identified patent and that said Letters Patent is hereby corrected as shown below:

On the Title Page

Item (30), Foreign Application Priority Data    "Apr. 4, 2014 (SE) ............ 1450413" should read --Apr. 4, 2014 (SE) ............ 1450413-8--

Signed and Sealed this
Seventh Day of May, 2019

Andrei Iancu
*Director of the United States Patent and Trademark Office*